United States Patent [19]

Kim et al.

[11] Patent Number: 4,988,812

[45] Date of Patent: Jan. 29, 1991

[54] AQUEOUS PROCESS FOR THE PREPARATION OF 5-METHYL-N-(ARYL)-1,2,4-TRIAZOLO(1,5-A)PYRIMIDINE-2-SULFONAMIDES

[75] Inventors: Kay K. Kim; Richard C. Krauss, all of Midland, Mich.; Jon A. Orvik

[73] Assignee: Dow Elanco, Indianapolis, Ind.

[21] Appl. No.: 432,241

[22] Filed: Nov. 6, 1989

[51] Int. Cl.$^5$ ............................................. C07D 487/04
[52] U.S. Cl. .................................. 544/263; 548/263.8
[58] Field of Search .......................................... 544/263

[56] References Cited

U.S. PATENT DOCUMENTS

| | | | |
|---|---|---|---|
| 2,444,606 | 7/1948 | Heimbach et al. | 544/263 |
| 4,617,303 | 10/1986 | Eicken et al. | 544/263 |
| 4,650,892 | 3/1987 | Kleschick et al. | 544/263 |
| 4,734,123 | 3/1988 | Monte | 544/263 |
| 4,755,212 | 7/1988 | Kleschick et al. | 544/263 |
| 4,854,964 | 8/1989 | Jelich | 544/263 |
| 4,886,883 | 12/1989 | Keschick et al. | 544/263 |

FOREIGN PATENT DOCUMENTS

| | | | |
|---|---|---|---|
| 2273980 | 11/1987 | Japan | 544/263 |
| 3267772 | 11/1988 | Japan | 544/263 |

*Primary Examiner*—Donald G. Daus
*Attorney, Agent, or Firm*—Craig E. Mixan; Ronald G. Brookens

[57] ABSTRACT

5-Methyl-N-(aryl)-1,2,4-triazolo[1,5-a]-pyrimidine-2-sulfonamides are prepared by the cyclization of N-(3-(((aryl)amino)sulfonyl)-1H-1,2,4-triazol-5-yl)amines with 4-methoxy-3-butene-2-one or its synthetic equivalents in the presence of an aqueous base. By controlling the pH of the condensation between 8.5 and 10.5, by-product formation can be substantially reduced.

9 Claims, No Drawings

AQUEOUS PROCESS FOR THE PREPARATION OF 5-METHYL-N-(ARYL)-1,2,4-TRIAZOLO(1,5-A)PYRIMIDINE-2-SULFONAMIDES

FIELD OF THE INVENTION

The present invention relates to a process for the preparation of 5-methyl-N-(aryl)-1,2,4-triazolo-[1,5-a]pyrimidine-2-sulfonamides by the aqueous alkaline cyclization of N-(3-(((aryl)amino)sulfonyl)-1H-1,2,4-triazol-5-yl)amines with 4-methoxy-3-butene-2-one or a precursor thereof.

BACKGROUND OF THE INVENTION

Aryl substituted 5-methyl-N-(aryl)-1,2,4-triazolo [1,5-a]pyrimidine-2-sulfonamides (I),

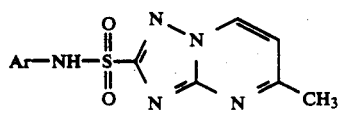

such as those described in U.S. Pat. No. 4,755,212, are valuable herbicides for the selective control of weeds in agronomic crops. U.S. Pat. No. 4,734,123 recommends as the final step in the preparation of these compounds the cyclization of N-(3-(((aryl)amino)sulfonyl)-1H-1,2,4-triazol-5-yl)amines (II) with appropriately substituted 1,3-dicarbonyl compounds or their synthetic equivalents, for example:

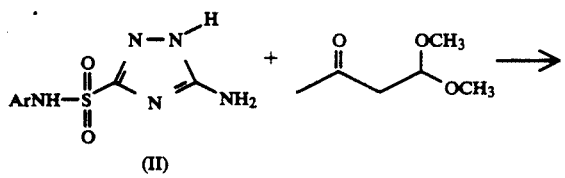

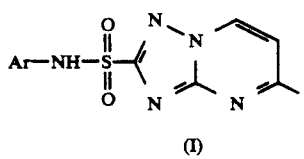

Accordingly the cyclizations may be conducted under acidic, neutral or basic conditions in a variety of solvents including, for example, acetic acid, ethanol, butanol, dimethylformamide, dimethylsulfoxide or tetrahydrofuran. Among the difficulties encountered with such cyclizations are depressed yields associated with decomposition of both product and starting material and with formation of undesired isomers, e.g., the 7-methyl isomer.

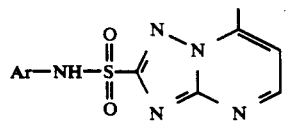

The discovery of a high yield process with a high selectivity to the desired 5-methyl isomer would be of great interest. Furthermore, the replacement of flammable and toxic organic solvents with environmentally benign water would be of considerable benefit.

SUMMARY OF THE INVENTION

The present invention relates to a process for preparing 5-methyl-N-(aryl)-1,2,4-triazolo[1,5-a]pyrimidine-2-sulfonamides of the formula:

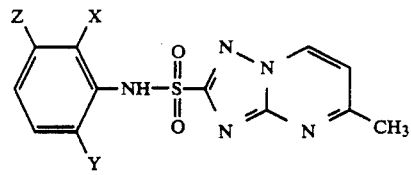

wherein
X represents F, Cl, Br or $C_1$–$C_4$ alkyl,
Y represents F, Cl, Br or $NO_2$, and
Z represents H, $C_1$–$C_4$ alkyl or $C_1$–$C_4$ alkoxy,
which comprises contacting an N-(3-(((aryl)amino)-sulfonyl)-1H-1,2,4-triazol-5-yl) amine of the formula:

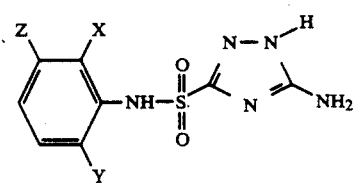

wherein
X, Y and Z are as previously defined, with 4-methoxy-3-butene-2-one or a synthetic equivalent thereof in an aqueous alkaline medium and controlling the pH of the mixture between about 8.5 and about 10.5.

By conducting the cyclization in water at a pH between about 8.5 and about 10.5, a high yield of the desired 5-methyl isomer with very little contaminating 7-methyl isomer is obtained.

DETAILED DESCRIPTION OF THE INVENTION

As used herein, the terms "$C_1$–$C_4$ alkyl" and "$C_1$–$C_4$ alkoxy" refer to straight-chained or branched hydrocarbon groups of up to four carbon atoms, provided that all substituent groups are sterically compatible with each other. The term "sterically compatible" is employed to designate substituent groups which are not affected by steric hindrance as this term is defined in "The Condensed Chemical Dictionary", 7th edition, Reinhold Publishing Co., N.Y. page 893 (1966) which definition is as follows: "steric hindrance: A characteristic of molecular structure in which the molecules have a spatial arrangement of their atoms such that a given reaction with another molecule is prevented or retarded in rate".

Sterically compatible may be further defined as reacting compounds having substituents whose physical bulk does not require confinement within volumes insufficient for the exercise of their normal behavior as discussed in Organic Chemistry of D. J. Cram and G. Hammond, 2nd edition, McGraw-Hill book Company, N.Y., page 215 (1964).

The preferred "$C_1$–$C_4$ alkyl" and "$C_1$–$C_4$ alkoxy" groups are —$CH_3$, —$CH_2CH_3$, —$OCH_3$ and —$OCH_2CH_3$. The most preferred group is —$CH_3$.

The N-(3-(((aryl)amino)sulfonyl)-1H-1,2,4-triazol-5-yl)amines (II) are known compounds and are described in U.S. Pat. No. 4,734,123. Of these starting materials, X and Y are preferably F or Cl. Most preferably, both X and Y are F. Z is preferably H.

4-Methoxy-3-butene-2-one is also a commercially available compound. Alternatively, 4-methoxy-3-butene-2-one can be generated in situ from appropriate precursors. For example, under basic conditions, 4,4-dimethoxybutanone eliminates methanol to generate 4-methoxy-3-butene-2-one.

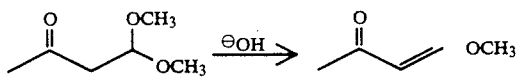

In the aqueous cyclization reaction, the N-(3-(((aryl-)amino)sulfonyl)-1H-1,2,4-triazol-5-yl) amine is condensed with 4-methoxy-3-butene-2-one or one of its synthetic equivalents, such as, for example, 4,4-dimethoxybutan-2-one.

In principal one equivalent of each reagent is required; in practice an excess of the 4-methoxy-3-butene-2-one or its synthetic equivalent is preferred. Generally, from 1.1 to 1.5 equivalents of the 4-methoxy-3-butene-2-one are employed, while about 1.2 equivalents are preferred.

Theoretically, the reaction can be conducted under acidic, neutral or basic conditions. It has been found, however, that under aqueous alkaline conditions, i.e., pH ≧8.5, the cyclization is highly selective to the desired 5-methyl isomer. Furthermore, at pH ≧11, the 4-methoxy-3-butene-2-one rapidly decomposes and the desired products, 5-methyl-N-(aryl)-1,2,4-triazolo-[1,5-a]pyrimidine-2-sulfonamides, are subject to hydrolysis, i.e., the reverse reaction of cyclization. Therefore, in order to insure high yields of the desired isomer under aqueous reaction conditions, it is critical to maintain the pH of the reaction between 8.5 and 10.5, more preferably between 8.5 and 9.5. The pH of the reaction can be controlled by continuous monitoring and adjusting as the reaction proceeds or, preferably, by using a buffer.

Suitable water-soluble bases that can be employed in the reaction include the alkali metal hydroxides, carbonates, and bicarbonates. Alkali metal, particularly sodium, hydroxide and carbonate and mixtures thereof are preferred as bases while carbonate and bicarbonate are preferred as buffers. The actual cyclization reaction is catalytic in base and the amount used is not critical: 0.2 to 1.0 equivalents of base are routinely employed for this condensation. Because of the relative acidity of the N-(3-(((aryl)amino)-sulfonyl)-1H-1,2,4-triazol-5-yl)amine (I) starting material, an additional equivalent of base is first required for neutralization.

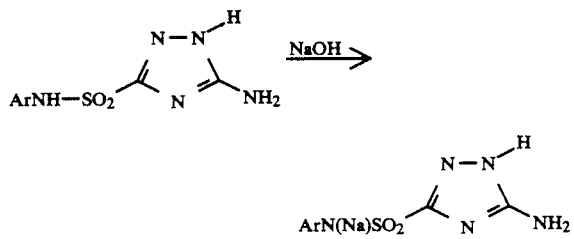

In a typical reaction, one equivalent of NaOH is added to neutralize the starting material and then about 0.2 equivalents of Na₂CO₃ are added to catalyze the cyclization. The Na₂CO₃ also serves to buffer the reaction medium. If the reactive 4-methoxy-3-butene-2-one is generated in situ, for example, by the reaction of 4,4-dimethoxybutanone with caustic, additional NaOH is not required since the reaction is catalytic in base.

The cyclization reaction is generally run from ambient temperature to about 90° C., preferably from 60° to 80° C.

The cyclization can be conducted in brine as well as in water. In fact, it is often convenient to perform the cyclization using crude N-(3-(((aryl)-amino)sulfonyl)-1H-1,2,4-triazol-5-yl) amine in the brine from which it can be prepared. In this process, the 5-methyl-N-(aryl)-1,2,4-triazolo[1,5-a]pyrimidine-2-sulfonamide is prepared in three steps from 5-amino-3-mercapto-1,2,4-triazole by:

(a) chlor-oxidation to form 5-amino-3-chlorosulfonyl-1,2,4-triazole:

(b) coupling with a substituted aniline to prepare N-(3-(((aryl)amino)sulfonyl)-1H-1,2,4-triazol-5-yl) amine; and (c) cyclization to give the desired product.

This is a particularly preferred process for the compound in which the aryl group is a 2,6-difluorophenyl moiety, viz., where X and Y are F, and Z is H.

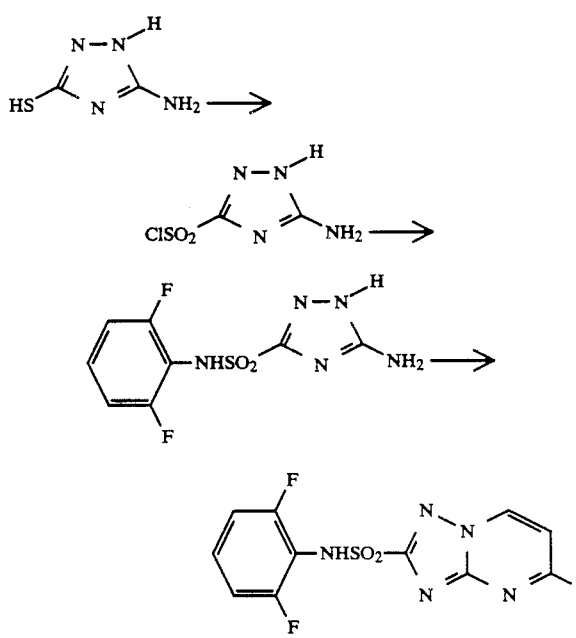

Each step may be conducted in water without isolation of the intermediate product.

In a typical example of this process, the N-(3-(((2,6-difluorophenyl)amino)sulfonyl)-1H-1,2,4-triazol-5-yl)amine is present in brine as a mixture of neutral compound and monosodium salt. To prepare this stream for cyclization, the pH is adjusted upward to a condition of mono- and disodium salts. This can be done, for example, by adjusting to pH to about 9.0 with Na₂CO₃. The cyclization is then initiated by addition of 1.2 equivalents of dimethoxybutane or methoxybutenone and held at a temperature of about 60° C. until conversion is complete. The product, as the monosodium salt, is insoluble in brine and precipitates during the course of the reaction. Purification may be accomplished by isolating the solid monosodium salt by filtration. Most impurities are rejected in the filtrate and wash. The conversion to neutral product is most advantageously accomplished by dissolution of the monosodium salt in hot water and by slow acidification to generate a crystalline precipitate. Acidification with acetic acid has proven very controllable, forming an acetate buffer which prevents acid hydrolysis of the product.

The following examples are presented to illustrate the invention and are not to be construed as a limitation thereon.

High pressure liquid chromatography (HPLC) was performed with one or the other of the following systems:

(a) on a chromatograph composed of an Hitachi L6200 pump, Kratos Spectroflow 757 variable wavelength detector at 214 nm, Spectra Physics SP 4290 integrator and Rheodyne 7125 injector with a 20 μl sample loop and a Jones Chromatography (Littleton Co.) Apex Octyl 5μ, 25 cm×4.6 mm reverse phase column in which the column was eluted at 1.8 cc/min with 8 volume percent acetonitrile and 0.1 volume percent $H_3PO_4$ in water: or (b) on a Hewlett Packard 1090 liquid chromatograph with UV detection at 214 nm, a 5 μl injector loop and a 25 cm Jones C-8 column in which the column was eluted at 1.8 cc/min with 19 volume percent acetonitrile and 0.1 volume percent $H_3PO_4$ in water.

EXAMPLE 1

Cyclization with Dimethoxybutanone and $Na_2CO_3$

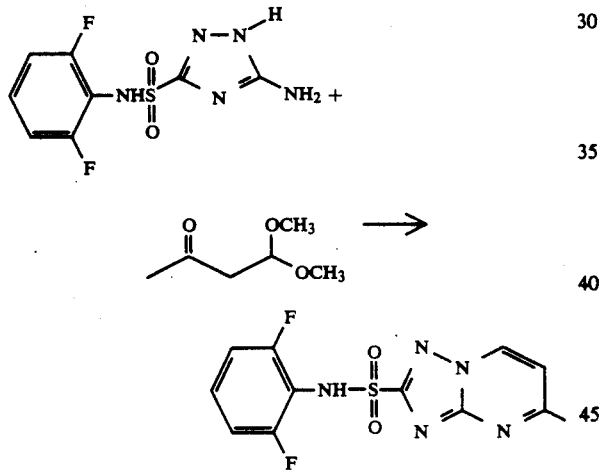

N-(3-(((2,6-difluorophenyl)amino)sulfonyl)-1H-1,2,4-triazol-5-yl)amine (2 grams (g), 7.3 millimoles) was suspended in 15 milliliters (mL) of water and was mixed with 1.2 g (10.9 millimoles) of $Na_2CO_3$. The slurry was heated to 50° C. and 1.44 g (10.9 millimoles) of 4,4-dimethoxybutan-2-one were added. After 5 hours (hrs), the reaction was judged complete by HPLC analysis and the solid product was filtered and washed with water. The wet cake was dissolved in water and acidified with 18 percent HCl until the pH reached about 4 at room temperature. The resulting slurry was stirred for 20 hrs and the product was recovered by filtration and dried to give 1.82 g of white solid with a 5-methyl/7-methyl isomer ratio of greater than 100.

EXAMPLE 2

Cyclization with Dimethoxybutanone and $Na_2CO_3$/NaOH

N-(3-(((2,6-difluorophenyl)amino)sulfonyl)-1H-1,2,4-triazol-5-yl)amine (27.5 g, 0.1 moles) dissolved in 100 mL of 1N NaOH solution (0.1 moles) was mixed with 5.3 g (0.05 moles) of $Na_2CO_3$ and the mixture was heated to 70° C. Dimethoxybutanone (19.8 g, 0.15 moles) was added and the mixture was stirred at 70° C. for 1 hr. The slurry was cooled and filtered, and the filter cake was washed with 100 mL of water and dried to yield 30.3 g (86 percent yield) of dry monosodium salt having a 5-methyl/7-methyl isomer ratio of 46.

EXAMPLE 3

Cyclization with Dimethoxybutanone and $Na_2CO_3$/NaOH

N-(3-(((2,6-difluorophenyl)amino)sulfonyl)-1H-1,2,4-triazol-5-yl)amine monohydrate (14.6 g, 0.05 moles) was combined with 50 mL of 1N NaOH (0.05 moles) and 5.2 g (0.05 moles) of $Na_2CO_3$ in 50 mL of water, and the mixture was heated to 80° C. to give a clear solution. The cyclization was initiated by the addition of 9.7 g (0.075 moles) of 4,4-dimethoxybutan-2-one. The reaction was maintained at 80° C. and monitored by HPLC. After about 10 minutes (min), the product rapidly precipitated in an oatmeal-like consistency. After 75 min, the reaction was complete and had a 5-methyl/7-methyl isomer ratio of 36. The reaction mixture was cooled to 3° C. and vacuum filtered to recover the monosodium salt. The filter cake was washed with about 30 mL of ice water and then resuspended in 100 mL of water. The suspension was heated to 90° C. to give a clear solution which was acidified by the dropwise addition of 4.5 g of acetic acid in 25 mL of water over 30 min. The resulting slurry was cooled to 3° C. and vacuum filtered. The product was washed with 50 mL of ice water and then 50 mL of methanol. After vacuum drying, the product weighed 14.2 g (87 percent yield) and had a purity of 99.8 percent by HPLC area percent analysis.

EXAMPLE 4

Cyclization with Dimethoxybutanone and $Na_2CO_3$/NaOH in Brine

N-(3-(((2,6-difluorophenyl)amino)sulfonyl)-1H-1,2,4-triazol-5-yl)amine (27.5 g, 0.1 moles) slurried in 77 g of water was mixed with 100 mL of 1N NaOH solution (0.1 moles) and 35 g of NaCl in a 500 mL 3-necked flask equipped with a thermometer, mechanical stirrer and a dropping funnel. Sodium carbonate (2.1 g, 0.02 moles) was added to the reaction mixture and the flask was heated to 60° C. 4,4-Dimethoxybutan-2-one (95 percent, 16 g, 0.12 moles) was added and the reaction mixture was stirred for 7 hrs at 60° C. After this time, all of the starting material had been consumed. The 5-methyl/7-methyl isomer ratio of the cooled reaction mixture was about 42. The white precipitate was filtered and the filter cake was washed with 100 mL of 20 percent NaCl solution. The wet cake was reslurried in 250 mL of water and neutralized by the dropwise addition of 1N HCl (100 mL, 0.1 moles) at 80° C. The mixture was cooled to 0° to 10° C. and the white solid product was isolated by filtration and dried at 90° C. under vacuum to a constant weight. A 91 percent yield (35.4 g) of product was obtained.

EXAMPLE 5

Preparation of 5-Methyl-N-(2,6-difluoro-phenyl)-1,2,4-triazolo[1,5-a]pyrimidine-2-sulfonamide from 5-Amino-3-mercapto-1,2,4-triazole without Intermediate Isolation

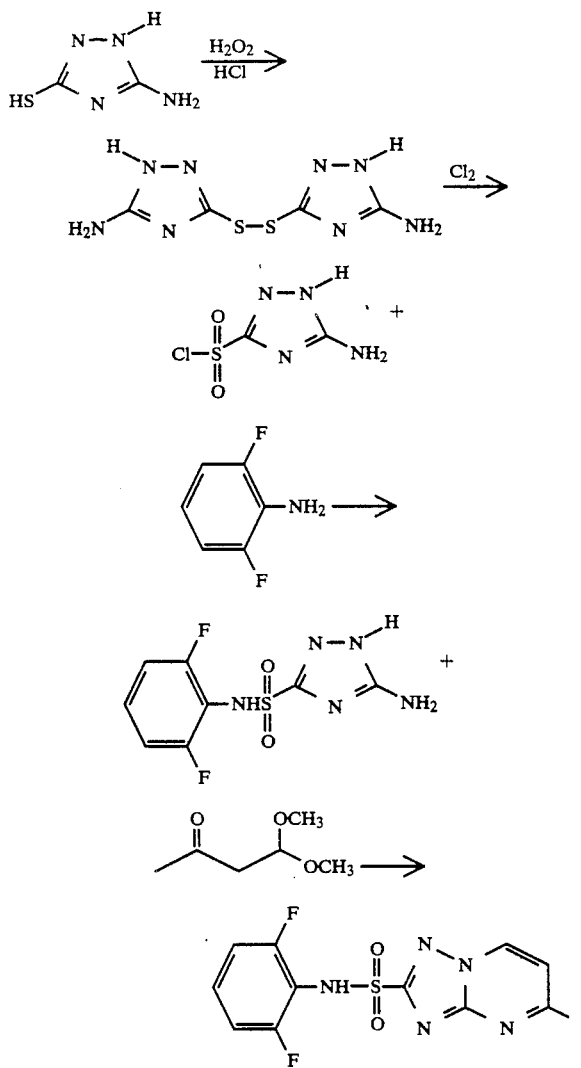

5-Amino-3-mercapto-1,2,4-triazole (23.5 g; 0.2 moles) and 160 mL of 6.25 N HCl (1.0 mole) were charged to a 500 mL 3-necked flask equipped with mechanical stirrer, dropping funnel and chlorine sparge tube. While maintaining the reaction temperature between 20° and 30° C., 12 g (0.105 moles) of 30 percent $H_2O_2$ were added dropwise over 10 min. Following the addition, the reaction was briefly warmed to 50° C. and then cooled to 0° C. using an ice/ethanol bath. Chlorine (39 g; 0.56 moles) was sparged into the reaction over 2 hrs at 0° C. and 60 mL of deionized water were added near the end of the reaction to maintain a stirrable slurry. After confirming complete conversion to the sulfonyl chloride by HPLC, 3 g of $Na_2S_2O_5$ were added to reduce any excess chlorine.

The 5-amino-3-chlorosulfonyl-1,2,4-triazole reaction mixture was added all at once to 310 g (2.4 moles) of wet 2,6-difluoroaniline and the reaction exothermed to about 45° C. Coupling was complete after 20 min The reaction was neutralized with 176 g (2.2 moles) of 50 percent NaOH to give a pH of 6.0. 2,6-Difluoroaniline was recovered by steam distillation using a Dean-Stark trap as receiver allowing the aqueous phase of the distillate to continuously return to the pot. After 283.5 g of 2,6-difluoroaniline were recovered, the resulting slurry contained N-(3-(((2,6-difluorophenyl)amino)sulfonyl)-1H-1,2,4-triazol-5-yl)amine with only a trace of the aniline remaining. The slurry was cooled to 60° C. in preparation for cyclization.

The pH of the slurry was adjusted from 5.3 to 9.2 by the addition of 10.6 g of $Na_2CO_3$. The cyclization was initiated by heating to 60° C. and by adding 34 g 0.25 moles) of 95 percent dimethoxybutanone. The temperature was held at 60° C. for 4 hrs, during which time the product precipitated. After 4 hrs, the reaction was cooled to 20° C. and vacuum filtered. The filter cake was washed with 200 mL of 20 percent NaCl brine and was reslurried in 300 mL of water. After heating to 90° C., the slurry was acidified by the dropwise addition of 100 mL of 2N HCl over 1 hr. After cooling to room temperature, the solid product was collected by vacuum filtration and washed with about 200 mL of water. Vacuum drying at 100° C. gave 53.3 g of 5-methyl-N-(2,6-difluorophenyl)-1,2,4-triazolo[1,5-a]-pyrimidine-2-sulfonamide.

What is claimed is:

1. A process for preparing 5-methyl-N-(aryl)-1,2,4-triazolo (1,5-a)pyrimidine-2-sulfonamides of the formula

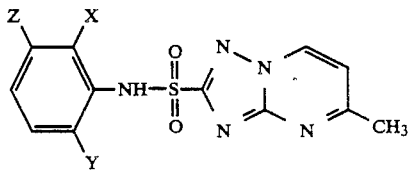

wherein
X represents F, Cl, Br or $C_1$–$C_4$ alkyl,
Y represents F, Cl, Br or $NO_2$, and
Z represents H, $C_1$–$C_4$ alkyl or $C_1$–$C_4$ alkoxy,
consisting essentially of contacting an N-(3-(((aryl)amino)sulfonyl)-1H-1,2,4-triazol-5-yl)amine amine of the formula

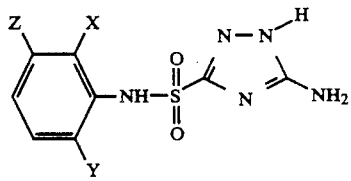

wherein
X, Y and Z are as previously defined, with 4-methoxy-3-butene-2-one or 4,4-dimethoxybutan-2-one in the presence of an aqueous solution of base while controlling the pH of the mixture between about 8.5 and about 10.5.

2. The process of claim 1 in which X and Y represent F and Z represents H.

3. The process of claim 1 in which the base is an alkali metal hydroxide, carbonate or bicarbonate or mixtures thereof.

4. The process of claim 1 in which the pH is controlled between 8.5 and 9.5.

5. The process of claim 1 in which the pH of the reaction mixture is controlled by the use of a buffer.

6. The process of claim 5 in which the buffer is an alkali metal carbonate or bicarbonate.

7. The process of claim 1 in which the N-(3-(((aryl)amino)sulfonyl-1H-1,2,4-triazol-5-yl)amine is prepared by coupling a substituted aniline with 5-amino-3-chlorosulfonyl-1,2,4-triazole in an aqueous medium.

8. The process of claim 7 in which the substituted aniline is 2,6-difluoroaniline.

9. The process of claim 7 in which the N-(3-(((aryl)amino)sulfonyl)-1H-1,2,4-triazol-5-yl)amine is used in the brine from which it is prepared without isolation.

* * * * *